US012605309B2

(12) United States Patent
Gu et al.

(10) Patent No.: US 12,605,309 B2
(45) Date of Patent: Apr. 21, 2026

(54) PRESSED POWDER PRODUCT AND METHOD FOR PREPARING THE SAME

(71) Applicant: Shanghai Marshmallowmakeup Biotech Corp., Ltd, Shanghai (CN)

(72) Inventors: Hongwei Gu, Shanghai (CN); Haifeng Qin, Shanghai (CN); Huaicheng Yu, Shanghai (CN)

(73) Assignee: Shanghai Marshmallowmakeup Biotech Corp., Ltd, Shanghai (CN)

( * ) Notice: Subject to any disclaimer, the term of this patent is extended or adjusted under 35 U.S.C. 154(b) by 384 days.

(21) Appl. No.: 18/201,776

(22) Filed: May 25, 2023

(65) Prior Publication Data

US 2024/0156689 A1 May 16, 2024

(30) Foreign Application Priority Data

Nov. 15, 2022 (CN) .......................... 202211423577.4

(51) Int. Cl.
| | |
|---|---|
| *A61K 8/02* | (2006.01) |
| *A61K 8/25* | (2006.01) |
| *A61Q 1/08* | (2006.01) |
| *A61Q 1/10* | (2006.01) |
| *A61Q 1/12* | (2006.01) |

(52) U.S. Cl.
CPC ................ *A61K 8/022* (2013.01); *A61Q 1/12* (2013.01); *A61K 2800/412* (2013.01); *A61K 2800/42* (2013.01); *A61K 2800/592* (2013.01); *A61K 2800/805* (2013.01)

(58) Field of Classification Search
CPC .... A61K 8/022; A61K 2800/592; A61K 8/25; A61K 2800/52; A61K 2800/651; A61Q 1/12; A61Q 1/10
See application file for complete search history.

(56) References Cited

U.S. PATENT DOCUMENTS

| | | | | |
|---|---|---|---|---|
| 2008/0274071 A1 * | 11/2008 | Kaplan | ................... | A61K 8/72 |
| | | | | 424/70.11 |
| 2020/0095441 A1 | 3/2020 | Urashima et al. | | |

FOREIGN PATENT DOCUMENTS

| | | | | |
|---|---|---|---|---|
| CN | 113208938 | | * | 8/2021 |
| CN | 113208938 A | | * | 8/2021 |
| FR | 2759941 A1 | | | 8/1998 |
| JP | 61207318 | | * | 9/1986 |
| JP | 61207318 A | | * | 9/1986 |
| JP | 2016216416 A | | | 12/2016 |
| JP | 2016216678 A | | | 12/2016 |
| JP | 2019505497 A | | | 2/2019 |
| JP | 2019038769 A | | | 3/2019 |
| WO | WO2019156165 A1 | | | 8/2019 |
| WO | WO2022008385 A1 | | | 1/2022 |

OTHER PUBLICATIONS

European search report of EP23176074.5.

* cited by examiner

*Primary Examiner* — Mina Haghighatian

(57) ABSTRACT

A pressed powder product and a method for preparing the same are provided. The pressed powder product includes a pressed powder layer, an ink absorbing layer and a pattern layer. The pattern layer is obtained by printing. The ink absorbing layer is formed by spraying an ink-absorbing paint on the pressed powder layer. The ink-absorbing paint includes 0.5% to 10% by weight of an oil controlling agent, 0.5% to 20% by weight of a color developing agent, 55% to 98.5% by weight of a solvent, and 0.5% to 10% by weight of a stabilizer. The method for preparing the pressed powder product includes: uniformly mixing an oil controlling agent, a color developing agent, a solvent, and a stabilizer to obtain the mixture; spraying the mixture on a pressed powder layer, and drying to obtain a semi-manufactured pressed powder product; and, printing a pattern on the semi-manufactured pressed powder product.

8 Claims, 1 Drawing Sheet

(COMPARATIVE EMBODIMENT)

PRESSED POWDER PRODUCT AND METHOD FOR PREPARING THE SAME

CROSS-REFERENCE TO RELATED APPLICATIONS

This application claims priority to Chinese patent application No. 202211423577.4, filed on Nov. 15, 2022, the content of which is hereby incorporated by reference in its entirety.

TECHNICAL FIELD

The present disclosure relates to the field of the method for preparing a pressed powder product, in particular, to a pressed powder product and a method for preparing the same.

BACKGROUND

A pressed powder product, such as a pressed powder, a cheek color, an eye shadow and the like, are products produced by compression molding, especially the pressed powder. The pressed powder is produced by mixing materials for preparing the pressed powder, and molding the materials with a powder press machine.

To improve functional performances of the pressed powder, and to further improve a sales volume of the pressed powder, merchants usually dispose some patterns on the pressed powder to attract consumers. Conventionally, the pattern on the surface of the pressed powder product is a small simple pattern disposed on the surface by spraying white slurry on the surface of the powder product.

Conventionally, the pattern on the surface of the pressed powder product is a single color, the pattern is simple, and the sprayed pattern may be broken.

SUMMARY

In order to improve the integrity of a pattern on the surface of a pressed powder product, the present disclosure provides a pressed powder product having an unbroken pattern on the surface and a method for preparing the same.

In a first aspect, the present disclosure provides a pressed powder product having an unbroken pattern on the surface.

The pressed powder product having an unbroken pattern on the surface, including a pressed powder layer, an ink absorbing layer, and a pattern layer. The pattern layer is prepared by printing with an ink. The ink absorbing layer is formed by spraying an ink-absorbing paint on the pressed powder layer. The ink-absorbing paint includes 0.5% to 10% by weight of an oil controlling agent, 0.5% to 20% by weight of a color developing agent, 55% to 98.5% by weight of solvent, and 0.5% to 10% by weight of a stabilizer. The oil controlling agent includes hydroxyapatite and kaolin particles, and a weight ratio of the hydroxyapatite to the kaolin particles is (5-6):(1-2).

In some embodiments, the color developing agent is silicon dioxide.

In some embodiments, the stabilizer is calcium carbonate.

In some embodiments, the solvent is any one selected from ethanol and isopropanol. In some embodiments, the solvent is ethanol.

In some embodiments, the oil controlling agent consists of the hydroxyapatite and the kaolin particles, and the weight ratio of the hydroxyapatite to the kaolin particles is (5-6):(1-2). In some embodiments, the weight ratio of the hydroxyapatite to the kaolin particles is 5:1.

In some embodiments, the kaolin particles are calcined kaolin particles.

In order to improve integrity of a pattern on the surface of the pressed powder product, the present disclosure provides a pattern layer on a surface of the pressed powder product. The pattern layer is made by printing with ink. In order to reduce permeation of the ink into the pressed powder product, an ink absorbing layer is disposed between the pattern layer and the pressed powder product. Therefore, permeation of the ink from the pattern layer to the pressed powder layer can be reduced, which prevents the pressed powder product from being affected. An oil controlling agent in the ink absorbing layer can be composed of kaolin particles and hydroxyapatite. The kaolin particles has a loose porous structure, which is beneficial for improving a porous volume of the ink absorbing layer and a bulk density of the ink absorbing layer, thereby facilitating ink absorption. The hydroxyapatite facilitates reducing permeation of the ink to the pressed powder layer. The color developing agent facilitates improving integrity of the pattern layer. The oil controlling agent and the color developing agent cooperates with each other, on the one hand can improve the integrity and diversity of the pattern on the surface of the pressed powder product, on the other hand can protect the pressed powder product from permeation of the ink to the pressed powder layer.

In some embodiment, the hydroxyapatite is a modified hydroxyapatite. The modified hydroxyapatite is prepared by following steps: infusing a chitosan quaternary ammonium salt in a butylbenzene emulsion to obtain a pretreated chitosan quaternary ammonium salt, and mixing the pretreated chitosan quaternary ammonium salt with the hydroxyapatite to obtain the modified hydroxyapatite.

In some embodiments, a mass ratio of the chitosan quaternary ammonium salt to the hydroxyapatite is in a range of 1:4 to 1:6.

The chitosan quaternary ammonium salt not only has representative characteristics of quaternary ammonium slats such as antibacterial property, moisture absorption and moisture retention, but also has characters of the chitosan such as good film-forming performance and biocompatibility. By adhering the hydroxyapatite outside the chitosan quaternary ammonium salt, an oil controlling layer can be formed outside the chitosan quaternary ammonium salt by the hydroxyapatite. In this way, by the technical solution described above, the ink absorbing layer has antibacterial property on the basis of adjusting the permeation of the ink of the ink absorbing layer, so that antibacterial property of the pressed powder product can be improved.

In some embodiments, the chitosan quaternary ammonium salt is a modified chitosan quaternary ammonium salt, and the modified chitosan quaternary ammonium salt is the chitosan quaternary ammonium salt subjected to a surface treatment with octyltriethoxysilane.

In some embodiments, a particle size of the chitosan quaternary ammonium slat is in a range of 50 nanometers to 100 nanometers.

In this way, after the chitosan quaternary ammonium slat is treated with the octyltriethoxysilane, a surface of the chitosan quaternary ammonium slat can be lipophilic and has hydrophobicity, which facilitates improving hydrophobicity of the ink absorbing layer.

In some embodiments, the chitosan quaternary ammonium salt is subjected to an etching treatment with an organic solvent.

In this way, since the chitosan quaternary ammonium salt is subjected to an etching treatment with an organic solvent, a specific surface area of the chitosan quaternary ammonium salt can be improved, so that roughness of the surface of the chitosan quaternary ammonium salt can be improved. Thus, more butylbenzene emulsion can be adhered in the infusing process, and thus more hydroxyapatite can be adhered, thereby improving a density of the oil controlling layer and improving an oil controlling performance of the oil controlling layer. Therefore, the permeation of the ink to the pressed powder product can be reduced.

In some embodiments, the kaolin particles includes 20% to 25% by weight of kaolin particles having particle sizes in arrange of 0.5 micrometers to 0.8 micrometers, 30% to 35% by weight of kaolin particles having particle sizes in a range of 0.8 micrometers to 1.5 micrometers, 25% to 30% by weight of kaolin particles having particle sizes in a range of 1.5 micrometers to 2.0 micrometers, and 15% to 20% by weight of kaolin particles having particle sizes in a range of 2.0 micrometers to 2.5 micrometers.

In this way, since kaolin particles having different particle sizes are added in the pressed powder product of the present disclosure, the kaolin particles distributes in the ink absorbing layer and fill in interspaces in the ink absorbing layer. Therefore, a density of the ink absorbing layer can be improved, so that permeation of the ink in the pressed powder product can be reduced and the integrity of the pattern can be improved.

In some embodiments, the ink-absorbing paint further includes 1% to 2% by weight of an adhesive. The adhesive is at least two selected from silicon dioxide, polyvinyl alcohol, and ethylene vinyl acetate copolymer.

In this way, since adding of the adhesive improves adhesiveness between components of the ink absorbing layer, the oil controlling performance of the ink absorbing layer and color developing of the ink absorbing layer can be better. Therefore, the integrity of the pattern can be improved, the density of the ink absorbing layer can be improved, and permeation of the ink to the pressed powder product can be reduced.

In some embodiments, the adhesive consists of silicon dioxide, polyvinyl alcohol, and ethylene vinyl acetate copolymer, and a weight ratio of the silicon dioxide, polyvinyl alcohol, and ethylene vinyl acetate copolymer is in a range of (5-6):(3-4):(1-2).

In this way, the silicon dioxide, polyvinyl alcohol, and ethylene vinyl acetate copolymer work together, and have good synergistic effects. The polyvinyl alcohol can improve a dispersity of the silicon dioxide and the ethylene vinyl acetate copolymer in the ink absorbing layer, improve the uniformity of the ink absorbing layer, and make the ink disperse more uniformly on the surface of the ink absorbing layer. The polyvinyl alcohol and the ethylene vinyl acetate copolymer match well in aspects of particle size and shape. The polyvinyl alcohol and the ethylene vinyl acetate copolymer cooperate with each other, which facilitates effectively adjusting diffusion and permeation of the ink, reducing permeation of the ink to the pressed powder layer, and improving stability of the pattern layer at the same time.

In a second aspect, the present disclosure provides a method for preparing a pressed powder product having an unbroken pattern on the surface.

A method for preparing a pressed powder product having an unbroken pattern on the surface includes the following steps: preparing a mixture, which includes steps of uniformly mixing an oil controlling agent, a color developing agent, a solvent, and a stabilizer to obtain the mixture;

preparing an ink absorbing layer, which includes steps of spraying the mixture on a pressed powder layer, and drying to obtain a semi-manufactured pressed powder product; and, preparing a pressed powder product, which includes steps of printing a pattern on the semi-manufactured pressed powder product. The mixture includes 0.5% to 10% by weight of an oil controlling agent, 0.5% to 20% by weight of a color developing agent, 55% to 98.5% by weight of a solvent, and 0.5% to 10% by weight of a stabilizer, and the oil controlling agent comprises hydroxyapatite and kaolin particles, and a weight ratio of the hydroxyapatite to the kaolin particles is (5-6):(1-2).

In some embodiments, the mixture further includes an adhesive.

In some embodiments, the mixture includes 1% to 2% by weight of the adhesive, the adhesive is at least two selected from the group consisting of silicon dioxide, polyvinyl alcohol, and ethylene vinyl acetate copolymer.

In some embodiments, the pressed powder layer can be a surface of a pressed powder product such as a pressed powder, an eye shadow, a cheek color and the like.

In some embodiments, a drying process is drying in an oven, a temperature of the drying process is in a range of 40 degrees centigrade to 50 degrees centigrade, and a time of the drying process is in a range of 1 hour to 2 hours.

In this way, since an ink absorbing layer is sprayed on a pressed powder layer in the present disclosure, on one hand it is beneficial for improving the integrity and the diversity of the pattern on the surface of the pressed powder product, and on the other hand the oil controlling agent added in the ink absorbing layer is beneficial for reducing permeation of the ink of the pattern to the pressed powder layer.

The present disclosure has the following beneficial effects.

In the present disclosure, the pressed powder product having an unbroken pattern on the surface is provided with a powder layer, an ink absorbing layer, and a pattern layer. The pattern layer can facilitate printing a required pattern with ink. The ink absorbing layer can be defined as an intermedium layer, and facilitate connecting the pattern layer to the pressed powder layer. By adjusting permeation or absorption of the ink, the ink absorbing layer can facilitate reducing permeation of the ink to the pressed powder layer, thereby reducing effect of a printed pattern to the pressed powder product.

In the present disclosure, by adding an adhesive in to the ink absorbing layer of the pressed powder product having an unbroken pattern on the surface, adhesiveness between components of the ink absorbing layer can be improved, which can promote an oil controlling performance of the hydroxyapatite and a color developing performance of the color developing agent. Therefore, the integrity of the pattern can be improved, density of the ink absorbing layer can be improved at the same time, and the permeation of the ink to the pressed powder product can be reduced.

DETAILED DESCRIPTION

Figures 1, 2:
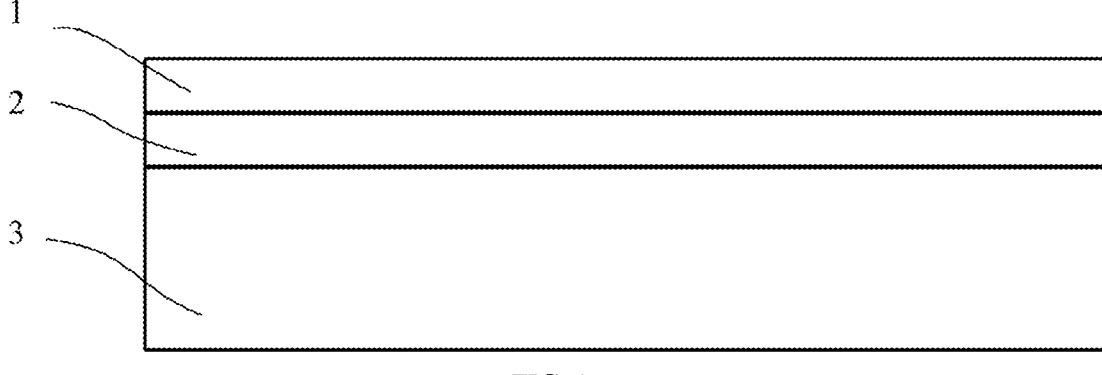
FIG. 1 is a structural schematic diagram of a pressed powder product in an embodiment of the present disclosure (1 represents a pattern layer, 2 represents an ink absorbing layer, and 3 represents a pressed powder layer).
FIG. 2 is a structural schematic diagram of a pressed powder product in a comparative embodiment of the present disclosure (1' represents a pattern layer; and 3' represents a pressed powder layer).

The present disclosure will be described in details in combination with embodiments hereinafter.

First Embodiment

The pressed powder product having an unbroken pattern on the surface included a pressed powder layer 3, an ink absorbing layer 2, and a pattern layer 1 from the bottom to the top. In the present embodiment, the pressed powder layer was a pressed powder. The ink absorbing layer was formed by spraying an ink-absorbing paint on the pressed powder layer 3. Materials of the ink-absorbing paint were listed in Table 1. In the present embodiment, the oil controlling agent consisted of hydroxyapatite and kaolin particles, and a weight ratio of the hydroxyapatite to the kaolin particles was 5:1. The color developing agent was titanium dioxide, the stabilizer was calcium carbonate and the solvent was ethanol.

The method for preparing the pressed powder product having an unbroken pattern on the surface included the following steps.

Preparation of a mixture: an oil controlling agent, a color developing agent, a solvent, and a stabilizer were uniformly mixed to obtain the mixture.

Preparation of an ink absorbing layer: the mixture was sprayed on the pressed powder layer, and dried in an oven to obtain a semi-manufactured pressed powder product. A temperature of the drying process was 50 degrees centigrade, and a time of the drying process was 1 hour.

Preparation of a pressed powder product: a pattern was printed on the semi-manufactured powder product to obtain the pressed powder product.

TABLE 1

Materials of the ink-absorbing paint of the ink absorbing layer of the pressed powder product having an unbroken pattern in the first embodiment to the sixth embodiment.

| Component | % | | | | | |
| --- | --- | --- | --- | --- | --- | --- |
| | Embodiment 1 | Embodiment 2 | Embodiment 3 | Embodiment 4 | Embodiment 5 | Embodiment 6 |
| Oil controlling agent | 0.5 | 6 | 8 | 10 | 8 | 8 |
| Color developing agent | 0.5 | 6 | 15 | 20 | 15 | 15 |
| Stabilizer | 0.5 | 4 | 7 | 10 | 7 | 7 |
| Solvent | 98.5 | 84 | 70 | 60 | 69 | 68 |
| Adhesive | / | / | / | / | 1 | 2 |

Second Embodiment to Fourth Embodiment

The difference between the second embodiments to the fourth embodiments and the first embodiments is the materials of the ink-absorbing paint are the materials shown in FIG. 1.

Fifth Embodiment

The difference between the pressed powder product in the fifth embodiment and the third embodiment is the materials of the ink-absorbing paint were the materials shown in FIG.

1. In the fifth embodiment, the adhesive consisted of silicon dioxide and polyvinyl alcohol, and a weight ratio of the silicon dioxide to the polyvinyl alcohol was 1:1.

The method for preparing the pressed powder product having an unbroken pattern on the surface included the following steps.

Preparation of a mixture: an oil controlling agent, a color developing agent, a solvent, a stabilizer and an adhesive were uniformly mixed to obtain the mixture.

Preparation of an ink absorbing layer: the mixture was sprayed on the pressed powder layer, and dried in an oven to obtain a semi-manufactured pressed powder product. A temperature of the drying process was 50 degrees centigrade, and a time of the drying process was 1 hour.

Preparation of a pressed powder product: a pattern was printed on the semi-manufactured powder product to obtain the pressed powder product.

Sixth Embodiment

The difference between the pressed powder product in the sixth embodiment and the fifth embodiment is the materials of the ink-absorbing paint were the materials shown in FIG. 1.

Seventh Embodiment

The difference between the pressed powder product in the seventh embodiment and the fifth embodiment is the hydroxyapatite is a modified hydroxyapatite. The method for preparing the modified hydroxyapatite included the following steps: a chitosan quaternary ammonium salt was infused in a butylbenzene emulsion to obtain a pretreated chitosan quaternary ammonium salt, and the pretreated chitosan quaternary ammonium slat was mixed with the hydroxyapatite to obtain the modified hydroxyapatite. A weight ratio of the chitosan quaternary ammonium salt to the hydroxyapatite was 1:6.

Eighth Embodiment

The difference between the pressed powder product in the eighth embodiment and the seventh embodiment is the chitosan quaternary ammonium salt used for modifying the hydroxyapatite was a modified chitosan quaternary ammonium salt. The modified chitosan quaternary ammonium salt was obtained by subjecting the chitosan quaternary ammonium salt to a surface treatment with an octyltriethoxysilane. A particle size of the modified chitosan quaternary ammonium salt was 60 nanometers.

Ninth Embodiment

The difference between the pressed powder product in the ninth embodiment and the seventh embodiment is the chitosan quaternary ammonium salt used for modifying the hydroxyapatite was subjected to an etching treatment with an organic solvent. The etched chitosan quaternary ammonium salt was then subjected to a surface treatment with the octyltriethoxysilane.

Tenth Embodiment

The differences between the pressed powder product in the tenth embodiment and the ninth embodiment are that the kaolin particles included 25% by weight of kaolin particles having particle sizes in arrange of 0.5 micrometers to 0.8 micrometers, 35% by weight of kaolin particles having particle sizes in a range of 0.8 micrometers to 1.5 micrometers, 25% weight of kaolin particles having particle sizes in a range of 1.5 micrometers to 2.0 micrometers, and 15% by weight of kaolin particles having particle sizes in a range of 2.0 micrometers to 2.5 micrometers.

Eleventh Embodiment

The differences between the pressed powder product in the eleventh embodiment and the tenth embodiment are that the adhesive consisted of silicon dioxide, polyvinyl alcohol, and ethylene vinyl acetate copolymer, and a weight ratio of the silicon dioxide, polyvinyl alcohol, and ethylene vinyl acetate copolymer was in a range of 5:3:1.

Twelfth Embodiment

The differences between the pressed powder product in the twelfth embodiment and the tenth embodiment are that the adhesive consisted of silicon dioxide, polyvinyl alcohol, and ethylene vinyl acetate copolymer, and a weight ratio of the silicon dioxide, polyvinyl alcohol, and ethylene vinyl acetate copolymer was in a range of 6:4:2.

First Comparative Embodiment

Referring to FIG. 2, a pressed powder product having an unbroken pattern on the surface, which included a pressed powder layer 3' and a pattern layer 1' from the bottom to the top. In the present comparative embodiment, the pressed powder layer was a pressed powder.

Second Comparative Embodiment

The difference between a pressed powder product having an unbroken pattern on the surface in the second comparative embodiment and the first embodiment is the oil controlling agent was kaolin particles.

Third Comparative Embodiment

The difference between a pressed powder product having an unbroken pattern on the surface in the third comparative embodiment and the first embodiment is that the oil controlling agent consisted of the hydroxyapatite and the kaolin particles, and a weight ratio of the hydroxyapatite and the kaolin particles was 2:1.

Fourth Comparative Embodiment

The differences between a pressed powder product having an unbroken pattern on the surface in the fourth comparative embodiment and the first embodiment are that the oil controlling agent consisted of the hydroxyapatite and the kaolin particles, and a weight ratio of the hydroxyapatite and the kaolin particles was 8:1.

Methods for Testing
Method for Testing the Stability

The pressed powder products obtained in the first embodiment to the twelfth embodiment were placed under conditions of 50 degrees centigrade and −18 degrees centigrade for a month, and compared with products placed under condition of 25 degrees centigrade for a month. Appearance, color, integrity of the pattern, and feeling of smearing of the products were compared, so as to observe the stability of the pressed powder product. The results of the test were shown in Table 2.

Test of Ink Permeation

A moisture tester was used to test a water content of the pressed powder layer of the pressed powder products obtained in the first embodiment to the twelfth embodiment and the first comparative embodiment to the fourth comparative embodiment, so as to calculate a thickness of permeated ink, and the results of the test were shown in Table 2.

Test of Pattern Integrity

The pressed powder products obtained in the first embodiment to the twelfth embodiment and the first comparative embodiment to the fourth comparative embodiment were taken to observe integrity of the patterns, and the integrity of the patterns were scored (1-4, 5-7, or 8-10). The higher the score was, the better the integrity of the pattern was. The results of the test were shown in Table 2.

TABLE 2

Test results of the tests of the pressed powder product having an unbroken pattern on the surface in the first embodiment to the twelfth embodiment and the first comparative embodiment to the fourth embodiment

| No. | 50 degrees centigrade | −18 degrees centigrade | Thickness of permeated ink (micrometers) | Integrity of the pattern |
|---|---|---|---|---|
| Embodiment 1 | Normal | Normal | 1.4 | 8 |
| Embodiment 2 | Normal | Normal | 1.5 | 8 |
| Embodiment 3 | Normal | Normal | 1.2 | 8 |
| Embodiment 4 | Normal | Normal | 1.6 | 8 |
| Embodiment 5 | Normal | Normal | 0.8 | 9 |
| Embodiment 6 | Normal | Normal | 1 | 9 |
| Embodiment 7 | Normal | Normal | 0.7 | 9 |
| Embodiment 8 | Normal | Normal | 0.6 | 9 |
| Embodiment 9 | Normal | Normal | 0.5 | 9 |
| Embodiment 10 | Normal | Normal | 0.4 | 9 |
| Embodiment 11 | Normal | Normal | 0.2 | 9 |
| Embodiment 12 | Normal | Normal | 0.1 | 9 |
| Comparative Embodiment 1 | / | / | 4.1 | 3 |
| Comparative Embodiment 2 | / | / | 2.7 | 5 |
| Comparative Embodiment 3 | / | / | 2.3 | 6 |
| Comparative Embodiment 4 | / | / | 2.1 | 6 |

It could be concluded from the first embodiment to the fourth embodiment and the data in Table 2 that the integrity of the patterns of the pressed powder product in the first embodiment to the fourth embodiment was better. After placed at 50 degrees centigrade or −18 degrees centigrade for a month, states of the pressed powder products were normal, which indicated that the ink absorbing layer of the pressed powder product was better. In addition, the thickness of permeated ink to the pressed powder layer was less than 2 micrometers, having less effect on the pressed powder product. In view of this, the inventor speculated that providing an ink absorbing layer between the pattern layer and the pressed powder layer, on one hand could be beneficial for improving the integrity of the pattern, on the other hand could play a role of a buffer layer to reduce permeation of the ink to the pressed powder layer. Therefore, on premise that aesthetic of the pressed powder product is improved, effect of the ink to the pressed powder product could be reduced.

Referring to the fourth embodiment to the sixth embodiment and the data in Table 2, the integrity of the patterns of the pressed powder product in the fifth embodiment and the sixth embodiment were better. After placed at 50 degrees centigrade or −18 degrees centigrade for a month, states of the pressed powder products were normal. In addition, the thickness of permeated ink to the pressed powder layer was less than 1 micrometer. The inventor speculated that the difference between the fifth embodiment to the sixth embodiment and the fifth embodiment was that an adhesive was added in the ink-absorbing paint. The adhesive was composed of silicon dioxide and polyvinyl alcohol. Adding of the adhesive could make connection between the ink-absorbing paint and the other components more tightly. On premise that the density of the ink absorbing layer was improved, reducing a size of the porous between adjacent components could facilitate adjusting adsorption and permeation of the ink and improving stability of the pattern of the pressed powder product and reducing effect of the permeation of the ink on the pressed powder product.

Referring to the fifth embodiment, the seventh embodiment and the data in Table 2, the integrity of the pattern of the pressed powder product having an unbroken pattern on the surface obtained in the seventh embodiment was better. After placed at 50 degrees centigrade or −18 degrees centigrade for a month, states of the pressed powder products were normal. In addition, the thickness of permeated ink to the pressed powder layer was less than 1 micrometer. Compared with the fifth embodiment, the inventor speculated that in the seventh embodiment, the hydroxyapatite was coated on the chitosan quaternary ammonium salt, so that the chitosan quaternary ammonium salt could not only have representative characteristics of quaternary ammonium slats such as antibacterial property, moisture absorption and moisture retention, but also have characters of the chitosan such as good film-forming performance and biocompatibility; in addition, since the hydroxyapatite was adhered outside the chitosan quaternary ammonium salt, an oil controlling layer could be formed outside the chitosan quaternary ammonium salt, so that the ink absorbing layer could have an antibacterial property on the basis of adjusting the permeation of the ink of the ink absorbing layer.

Referring to the seventh embodiment, the eighth embodiment and the data in Table 2, the integrity of the pattern of the pressed powder product having an unbroken pattern on the surface obtained in the eighth embodiment was better. After placed at 50 degrees centigrade or −18 degrees centigrade for a month, states of the pressed powder products were normal. In addition, the thickness of permeated ink to the pressed powder layer was less than 0.7 micrometers. The inventor speculated that in the eighth embodiment, the chitosan quaternary ammonium salt was subjected to a hydrophobic treatment, so that the moisture absorption and the moisture retention of the chitosan quaternary ammonium salt could be reduced; at the same time, the hydroxyapatite on the surface of the quaternary ammonium salt could facilitate absorption of the ink, thereby reducing a thickness of the permeated ink in the pressed powder layer.

Referring to the seventh embodiment, the ninth embodiment and the data in Table 2, the integrity of the pattern of the pressed powder product having an unbroken pattern on the surface obtained in the ninth embodiment was better. After placed at 50 degrees centigrade or −18 degrees centigrade for a month, states of the pressed powder products were normal. In addition, the thickness of permeated ink to the pressed powder layer was less than 0.5 micrometers. The inventor speculated that in the ninth embodiment, the chitosan quaternary ammonium salt was subjected to an etching treatment with an organic solvent, so that a specific surface area of the chitosan quaternary ammonium slat could be improved and the surface of the chitosan quaternary ammonium salt could become coarser. Therefore, the hydroscopicity of the chitosan quaternary ammonium salt could be reduced, thereby reducing the thickness of the permeated ink in the pressed powder layer.

Referring to the ninth embodiment, the tenth embodiment and the data in Table 2, the integrity of the pattern of the pressed powder product having an unbroken pattern on the surface obtained in the tenth embodiment was better. After placed at 50 degrees centigrade or −18 degrees centigrade for a month, states of the pressed powder products were normal. In addition, the thickness of permeated ink to the pressed powder layer was less than 0.5 micrometers. The inventor speculated that in the tenth embodiment, since the kaolin particles included in the oil controlling agent of the ink-absorbing paint were kaolin particles having different particle sizes, the kaolin particles distributed in the ink absorbing layer and filled in interspaces in the ink absorbing layer. Therefore, a density of the ink absorbing layer could be improved, so that the permeation of the ink in the pressed powder product could be reduced and the integrity of the pattern could be improved.

Referring to the tenth embodiment to the twelfth embodiment and the data in Table 2, the integrity of the pattern of the pressed powder product having an unbroken pattern on the surface obtained in the eleventh embodiment the twelfth embodiment was better. After placed at 50 degrees centigrade or −18 degrees centigrade for a month, states of the pressed powder products were normal. In addition, the thickness of permeated ink to the pressed powder layer was less than 0.5 micrometers. The inventor speculated that in the eleventh embodiment and the twelfth embodiment, the adhesive in the ink-absorbing paint was composed of the silicon dioxide, the polyvinyl alcohol and the ethylene vinyl acetate copolymer, and the adhesive could match with other components in the ink-absorbing paint, so that the permeation of the ink to the pressed powder layer could be reduced and the diversity and the stability of the pattern layer could be improved.

The technical features of the above-mentioned embodiments can be combined arbitrarily. In order to make the description concise, not all possible combinations of the technical features are described in the embodiments. However, as long as there is no contradiction in the combination of these technical features, the combinations should be considered as in the scope of the present disclosure.

The above-described embodiments are only several implementations of the present disclosure, and the descriptions are relatively specific and detailed, but they should not be construed as limiting the scope of the present disclosure. It should be understood by those of ordinary skill in the art that various modifications and improvements can be made without departing from the concept of the present disclosure, and all fall within the protection scope of the present disclosure. Therefore, the patent protection of the present disclosure shall be defined by the appended claims.

What is claimed is:

1. A pressed powder product having a pattern on the surface, comprising a pressed powder layer, an ink absorbing layer, and a pattern layer, wherein the pattern layer is prepared by printing with an ink, the ink absorbing layer is formed by spraying an ink-absorbing paint on the pressed powder layer,

the ink-absorbing paint comprises 0.5% to 10% of an oil controlling agent by weight of the ink-absorbing paint, 0.5% to 20% of a color developing agent by weight of the ink-absorbing paint, 55% to 98.5% of a solvent by weight of the ink-absorbing paint, and 0.5% to 10% of a stabilizer by weight of the ink-absorbing paint, and the oil controlling agent comprises hydroxyapatite and kaolin particles, and a weight ratio of the hydroxyapatite to the kaolin particles is (5-6):(1-2), wherein the color developing agent is silicon dioxide, the solvent is any one selected from ethanol and isopropanol, and the stabilizer is calcium carbonate.

2. The pressed powder product of claim 1, wherein the hydroxyapatite is a modified hydroxyapatite, the modified hydroxyapatite is prepared by following steps:

infusing a chitosan quaternary ammonium salt in a butylbenzene emulsion to obtain a pretreated chitosan quaternary ammonium salt, and mixing the pretreated chitosan quaternary ammonium salt with the hydroxyapatite to obtain the modified hydroxyapatite.

3. The pressed powder product of claim 2, wherein the chitosan quaternary ammonium salt is a modified chitosan quaternary ammonium salt, and the modified chitosan quaternary ammonium salt is the chitosan quaternary ammonium salt subjected to a surface treatment with octyltriethoxysilane.

4. The pressed powder product of claim 1, wherein the kaolin particles comprises 20% to 25% by weight of kaolin particles having particle sizes in a range of 0.5 micrometers to 0.8 micrometers, 30% to 35% by weight of kaolin particles having particle sizes in a range of 0.8 micrometers to 1.5 micrometers, 25% to 30% by weight of kaolin particles having particle sizes in a range of 1.5 micrometers to 2.0 micrometers, and 15% to 20% by weight of kaolin particles having particle sizes in a range of 2.0 micrometers to 2.5 micrometers.

5. A method for preparing a pressed powder product, comprising, preparing a mixture, which comprises steps of uniformly mixing an oil controlling agent, a color developing agent, a solvent, and a stabilizer to obtain the mixture, wherein the mixture comprises 0.5% to 10% of the oil controlling agent by weight of the mixture, 0.5% to 20% of the color developing agent by weight of the mixture, 55% to 98.5% of the solvent by weight of the mixture, and 0.5% to 10% of the stabilizer by weight of the mixture, and the oil controlling agent comprises hydroxyapatite and kaolin particles, and a weight ratio of the hydroxyapatite to the kaolin particles is (5-6): (1-2);

preparing an ink absorbing layer, which comprises steps of spraying the mixture on a pressed powder layer, and drying to obtain a semi-manufactured pressed powder product; and preparing a pressed powder product, which comprises steps of printing a pattern on the semi-manufactured pressed powder product, wherein the color developing agent is silicon dioxide, the solvent is any one selected from ethanol and isopropanol, and the stabilizer is calcium carbonate.

6. The method for preparing the pressed powder product of claim 5, wherein the hydroxyapatite is a modified hydroxyapatite, the modified hydroxyapatite is prepared by following steps:

infusing a chitosan quaternary ammonium salt in a butylbenzene emulsion to obtain a pretreated chitosan quaternary ammonium salt, and mixing the pretreated chitosan quaternary ammonium salt with the hydroxyapatite to obtain the modified hydroxyapatite.

7. The method for preparing the pressed powder product of claim 6, wherein the chitosan quaternary ammonium salt is a modified chitosan quaternary ammonium salt, and the modified chitosan quaternary ammonium salt is the chitosan quaternary ammonium salt subjected to a surface treatment with octyltriethoxysilane.

8. The method for preparing the pressed powder product of claim 5, wherein the kaolin particles comprises 20% to 25% by weight of kaolin particles having particle sizes in a range of 0.5 micrometers to 0.8 micrometers, 30% to 35% by weight of kaolin particles having particle sizes in a range of 0.8 micrometers to 1.5 micrometers, 25% to 30% by weight of kaolin particles having particle sizes in a range of 1.5 micrometers to 2.0 micrometers, and 15% to 20% by weight of kaolin particles having particle sizes in a range of 2.0 micrometers to 2.5 micrometers.

* * * * *